(12) United States Patent
Kirst

(10) Patent No.: US 8,109,153 B2
(45) Date of Patent: Feb. 7, 2012

(54) METHOD FOR MEASURING AND/OR MONITORING A FLOW PARAMETER AND CORRESPONDING DEVICE

(75) Inventor: Michael Kirst, Lorrach (DE)

(73) Assignee: Endress + Hauser Flowtec AG, Reinach (CH)

( * ) Notice: Subject to any disclaimer, the term of this patent is extended or adjusted under 35 U.S.C. 154(b) by 230 days.

(21) Appl. No.: 12/450,984

(22) PCT Filed: May 14, 2008

(86) PCT No.: PCT/EP2008/055890

§ 371 (c)(1),
(2), (4) Date: Dec. 11, 2009

(87) PCT Pub. No.: WO2008/141986

PCT Pub. Date: Nov. 27, 2008

(65) Prior Publication Data

US 2010/0101333 A1    Apr. 29, 2010

(30) Foreign Application Priority Data

May 23, 2007   (DE) .......................... 10 2007 024 275

(51) Int. Cl.
*G01F 1/84* (2006.01)
(52) U.S. Cl. ................................................ 73/861.357
(58) Field of Classification Search ............ 73/861.355–861.357, 861.27–861.29
See application file for complete search history.

(56) References Cited

U.S. PATENT DOCUMENTS

| | | | |
|---|---|---|---|
| 5,121,639 A * | 6/1992 | McShane | 73/861.06 |
| 5,637,804 A | 6/1997 | Hansen | |
| 7,216,550 B2 | 5/2007 | Lesjak | |
| 7,412,903 B2 * | 8/2008 | Rieder et al. | 73/861.357 |

FOREIGN PATENT DOCUMENTS

| | | |
|---|---|---|
| DE | 39 23 409 | 1/1991 |
| DE | 101 38 323 C1 | 4/2003 |
| EP | 1 530 030 A2 | 5/2005 |
| GB | 2 379 507 | 3/2003 |
| WO | WO 00/22385 | 4/2000 |

* cited by examiner

*Primary Examiner* — Jewel V Thompson
(74) *Attorney, Agent, or Firm* — Bacon & Thomas, PLLC

(57) ABSTRACT

A method and apparatus for measuring and/or monitoring at least one flow parameter of a medium, which medium flows through a measuring tube, wherein the measuring tube is contacted by at least two transducer elements, by means of which the measuring tube is excitable to execute mechanical oscillations and by means of which mechanical oscillations of the measuring tube are receivable. Each of the at least two transducer elements is applied, offset in time, alternately, for exciting the measuring tube to execute mechanical oscillations and for receiving the mechanical oscillations of the measuring tube.

16 Claims, 3 Drawing Sheets

METHOD FOR MEASURING AND/OR MONITORING A FLOW PARAMETER AND CORRESPONDING DEVICE

TECHNICAL FIELD

The invention relates to a method for measuring and/or monitoring at least one flow parameter of a medium flowing through a measuring tube, wherein the measuring tube is contacted by at least two transducer elements, by means of which the measuring tube is excitable to execute mechanical oscillations and by means of which mechanical oscillations of the measuring tube are receivable. Furthermore, the invention relates to an apparatus for measuring and/or monitoring at least one flow parameter of a medium flowing through a measuring tube, which apparatus comprises at least one transducer element, via which transducer element both the measuring tube is excitable to execute mechanical oscillations, as well as, mechanical oscillations of the measuring tube are receivable. The flow parameter is, for example, the flow velocity, the volume flow or the mass flow of the medium. The medium is, for example, a liquid, a gas or, generally, a fluid, which is present in one or more phases.

BACKGROUND DISCUSSION

Known in the state of the art (e.g. in DE 10 2005 034 749 A1) is a Coriolis measuring device, which has two oscillation exciters and an oscillation receiver arranged centrally thereto. Through aging processes or through extraordinary parameters of the medium or the arising processes, changes can occur in the oscillation exciters, or in the oscillation receiver, such that a loss of accuracy of measurement is experienced. Furthermore, asymmetries in the oscillation excitation, or measurement uncertainties associated therewith connected in the oscillation detection, can occur, which, in given cases, as a result of aging phenomena, can be with, or without, material effect, as well as varying in time. Thus, it is necessary to test, or to check, the measuring device regularly.

WO 2006/036139 A1 describes a Coriolis measuring device, which has two oscillation exciters and two oscillation receivers, in each case, mounted parallel to the oscillation exciters. In order to be able to determine particular oscillation variables of the measuring tube, the two oscillation exciters are operated alternately. The oscillations arising, in such case, are, in each case, sensed by the oscillation receivers. In the case of this construction, there is provided, thus, a structurally conceived isolation between the oscillation excitation and the receiving of the oscillations.

Known in the state of the art are, furthermore, oscillation transducers, which serve both for the exciting of oscillations, as well as also for their detection (DE 103 51 310 A1). The associated electronics for operating the transducers are, in such case, embodied for particular tasks, i.e. either for excitation or for detection.

The application of transducer elements of piezoelectric material is described, for example, in the not published application DE 10 2005 059 070.

SUMMARY OF THE INVENTION

An object of the invention is to improve the measuring of a flow parameter toward the goal of recognizing asymmetries or aging phenomena and, in given cases, appropriately taking such into consideration.

The invention solves the task with a method wherein each of at least two transducer elements is applied, offset in time, alternately for exciting a measuring tube to execute mechanical oscillations and for receiving mechanical oscillations of the measuring tube. The at least two transducer elements undertake, thus, at different points in time, alternately the tasks of oscillation production and oscillation detection. The transducer elements are, for example, electrodynamic units or, for example, piezoelectric elements.

An embodiment of the method of the invention provides that the transducer element, offset in time, or simultaneously, is operated in a test mode and in a measuring mode. In the one case, there is a separation in time between the modes, i.e. either a test of the measuring device, or, especially, the mechanics of the measuring device, is performed or a normal measuring takes place. In the other case, the two modes are performed simultaneously, i.e. there is, quasi, a superpositioning of the two modes. In the case of the, in time, separated modes, in each case, a separate received signal is sensed from the measuring tube for the mechanical oscillations, and, in the case of the simultaneous embodiment of the two modes, a signal is received from the measuring tube, which represents a superpositioning of the respective effects of the two modes.

An embodiment of the method of the invention includes, that the transducer element in the test mode is supplied with a test exciter signal and in the measuring mode with a measuring exciter signal. The two modes differ in this embodiment at least in the fact that the at least one transducer element is supplied, in each case, with a special exciter signal, this meaning, thus, that the measuring tube is, in each case, excited to execute a special oscillation. The exciter signals are, preferably, electrical, alternating voltage signals.

An embodiment of the method of the invention provides that the test exciter signal and the measuring exciter signal differ from one another, at least as regards frequency. This embodiment is especially advantageous, when test and measuring modes take place at the same time, since the measuring tube is, in such case, excited to a superimposing of two oscillations, which then, as regards evaluation, also permits separation of the signals.

An embodiment of the method of the invention provides that, through the transducer element in combination with an oscillation driving electronics, the measuring tube is excited to execute mechanical oscillations, and that, through the transducer element in combination with an oscillation receiving electronics different from the oscillation driving electronics, mechanical oscillations of the measuring tube are received. In this embodiment, the transducer element is connected with two electronics means, each serving for a task of the transducer element, i.e. in the case of the producing of oscillations, the transducer element is operated by another electronics than in the case in which the transducer element is to receive oscillations. This means that each electronics can be designed especially for its task and that, thus, also the electronic variables are suitable therefor. Advantageous, thus, is that a transducer element can be used for oscillation production and oscillation detection, in each case, optimally, without that difficulties as regards the operating electronics are to be expected.

An embodiment of the method of the invention includes that, through at least two transducer elements, alternately, the measuring tube is excited to execute mechanical oscillations and mechanical oscillations are received from the measuring tube, wherein, in each case, one transducer element excites the measuring tube to execute mechanical oscillations and the other transducer element receives mechanical oscillations from the measuring tube. In this embodiment, two transducer elements are provided, which alternately serve, respectively, for oscillation excitement and detection. Thus, one element excites, and the other element, receives the oscillations, and, in the next step, the first element receives, while the second element produces the oscillations. This alternation then proceeds out into the future. Through this alternation, the properties of the oscillation transducer, or the measuring tube, can be monitored, ascertained and suitably taken into consideration for determining the flow parameters. This is, thus, also an example of the test mode.

An embodiment of the method of the invention provides that, through at least three transducer elements, individually or grouped, alternately the measuring tube is excited to execute mechanical oscillations and mechanical oscillations are received from the measuring tube, wherein, in each case, at least one transducer element excites the measuring tube to execute mechanical oscillations and at least one transducer element receives mechanical oscillations of the measuring tube. In this embodiment, three transducer elements are present, which alternately produce and receive the oscillations. These tasks are, then, in each case, performed by at least one transducer element. For example, two elements serve for oscillation production, while the third element receives or one element produces the oscillations and two elements receive. Which of the three elements performs which test, is, for example, suitably permutated. If, in the case of these different operating combinations, for example, different measured values occur for the flow parameters, then this is attributed to an asymmetry, whose value can then also be calculated correspondingly from the obtained variables.

An embodiment of the method of the invention includes that, in each case, alternately, through one of the three transducer elements, the measuring tube is excited to execute mechanical oscillations, and that the mechanical oscillations of the measuring tube are received by two transducer elements. The producing of the oscillations is, in each case, undertaken by one transducer element and in each case one of the three transducer elements is alternately this selected element, i.e. each element performs, alternately, the task of exciting the oscillations.

An embodiment of the method of the invention provides that, in each case, alternately, through, in each case, two of the three transducer elements, the measuring tube is excited to execute mechanical oscillations, and that the mechanical oscillations of the measuring tube are received by one transducer element. In an embodiment, there serve, alternating in time, in each case, two other transducer elements for oscillation excitement.

Furthermore, the invention achieves the task with an apparatus, which is embodied in such a manner, that the transducer element is connected with at least one oscillation driving electronics and one oscillation receiving electronics, wherein the oscillation driving electronics and the oscillation receiving electronics differ from one another, wherein the oscillation driving electronics effects, that the transducer element excites the measuring tube to execute mechanical oscillations, and wherein the oscillation receiving electronics effects, that the transducer element receives mechanical oscillations from the measuring tube. In the measuring device of the invention, thus, at least one transducer element, via which oscillations are both producible, as well as also receivable, is connected with two self-sufficient electronics, each of which is embodied for a special purpose, i.e. oscillation production or oscillation detection. The measuring device of the invention permits, thus, application of a transducer element optimal both for oscillation production, as well as also for receiving the oscillations. Especially, thus, also various measurements can be performed with the measuring device of the invention, without requiring that, for example, problematics with reference to electronic components must be taken into consideration.

An embodiment of the apparatus of the invention includes, that at least one test control unit is provided, which operates at least the transducer element in a test mode, and that at least one measurement control unit is provided, which operates at least the transducer element in a measuring mode. The at least one transducer element is, thus, operated by a test control unit and a measurement control unit, in each case in a different mode.

An embodiment of the apparatus of the invention includes, that at least two transducer elements are provided, via which transducer elements both the measuring tube is excitable to execute mechanical oscillations, as well as also via which transducer elements mechanical oscillations of the measuring tube are receivable.

An embodiment of the apparatus of the invention provides that at least three transducer elements are present, via which transducer elements both the measuring tube is excitable to execute mechanical oscillations, as well as also via which transducer elements mechanical oscillations of the measuring tube are receivable.

An embodiment of the apparatus of the invention includes, that at least two transducer elements are connected, in each case, with an oscillation driving electronics and an oscillation receiving electronics, wherein the oscillation driving electronics and the oscillation receiving electronics are, in each case, different from one another. In this embodiment, the measuring tube is contacted with two transducer elements, which, in turn, in each case, are connected with two electronics, i.e. a total of four electronics. In an additional embodiment, three transducer elements are provided, which, in each case, are individually connected with two different electronics.

An embodiment of the apparatus of the invention provides that two transducer elements are placed symmetrically to the third transducer element on the measuring tube. If, in this embodiment, the oscillation excitation in each case is performed by another transducer element or another group of transducer elements, then, from the different distributions, information can be won concerning the measuring tube and the transducer elements.

An embodiment of the apparatus of the invention includes, that at least one control unit is provided, which control unit, via at least one oscillation driving electronics and the therewith connected transducer element, excites the measuring tube to execute mechanical oscillations, and which control unit, via at least one oscillation receiving electronics and the therewith connected transducer element, receives the mechanical oscillations of the measuring tube. The control unit, thus, operates the transducer elements in such a manner, that they either produce, or detect, the oscillations, wherein, in each case, electronics especially adapted for each purpose is used. In such case, the control unit can, for example, rotate the tasks of, respectively, oscillation production and oscillation detection through the number of available transducer elements.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
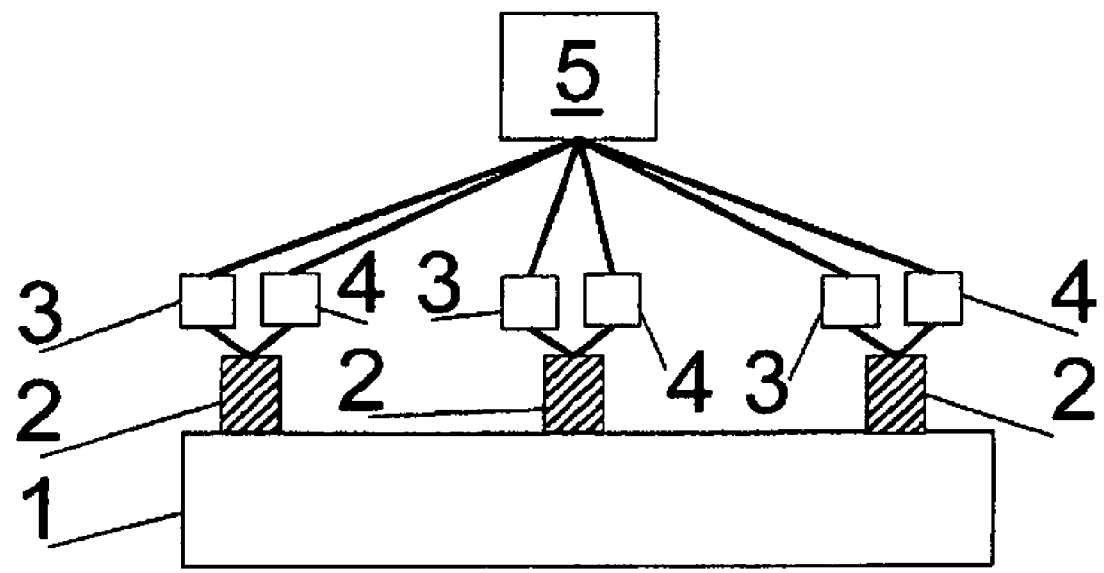
FIG. 1 is a schematic drawing of a first embodiment of a measuring device of the invention.

FIG. 1 shows an in line measuring device, especially an in line measuring device embodied as a Coriolis mass flow, and/or density, measuring device, which serves to register a mass flow of a medium flowing in a pipeline (not shown) and to provide a mass flow measured value instantaneously representing this mass flow. Thus, the flow parameter is, by way of example, the mass flow. The medium can be practically any flowable material, for example, a powder, a liquid, a gas, a vapor or the like. Alternatively or in supplementation, the shown measuring device can, in given cases, also be used to measure a density and/or a viscosity of the medium. The in line measuring device comprises therefor a measuring transducer of the vibration type, through which, during operation, the medium to be measured flows, i.e. a measuring tube 1 as well as a measuring device electronics 5 electrically connected with the measuring transducer 1. Measuring device electronics 5 is not shown here in detail, but, instead, only schematically, as a block. In advantageous manner, the measuring device electronics 5 is so designed, that it can, during operation of the in line measuring device, exchange measuring and/or other operating data with a measured value processing unit superordinated thereto, for example, a programmable logic controller (PLC), a personal computer and/or a work station, via a data transmission system, for example, a fieldbus system. Furthermore, the measuring device electronics 5 is so designed, that it can be supplied from an external energy supply, for example, also via the aforementioned fieldbus system.

The measuring device includes a measuring tube 1, which, during operation, vibrates, at least at times, and through which, during operation, a medium flows. Due to the oscillations of the measuring tube, flow parameters of the medium can be ascertained. Thus, for example, the Coriolis force induced in the measuring tube by the flowing medium is utilized, in order to ascertain the flow of the medium.

Alternatively or in supplementation, for example, also the density or the viscosity can be ascertained on the basis of the oscillation frequency, with which the vibrating measuring tube oscillates.

For producing the oscillations, or for their detection, there are provided, brought together in the drawing of the measuring apparatus, three transducer elements 2, which, for example, electrodynamically or by means of the piezo effect, provide a transducing between the mechanical oscillations and an electrical signal corresponding therewith. Two of the transducer elements 2 are, here, arranged symmetrically to a third element 2.

Each of the three transducer elements 2 is, in a first variant of the measuring of arrangement, connected with an oscillation driving electronics 3 and an oscillation receiving electronics 4. These two operating electronics 3, 4 are different relative to one another and serve either for exciting the mechanical oscillations of the measuring tube 1 (oscillation driving electronics 3) or for receiving mechanical oscillations from the measuring tube 1 (oscillation receiving electronics 4). I.e., each transducer element 2 has available two different operating electronics 3, 4, each of which is applied for performing a task (excitation and detection, respectively).

The operating electronics 3, 4 are each connected with the control unit 5, which assigns, alternately, to at least one of the three transducer elements 2, the task of producing the oscillations, or the task of their detection. By way of example, one transducer element serves for producing the oscillations and the two other transducer elements receive the oscillations. The control unit 5 uses, then, alternately, via the corresponding oscillation driving electronics 3, in each case, one transducer element 2 for oscillation production and receives from the two other transducer elements 2 the electrical signals associated with the oscillations. From the received signals, combined with the position of the exciting transducer element, information can be gained concerning the symmetry, or concerning the character, of the transducer elements, and, on the basis of such information, also the flow parameters can be more exactly ascertained.

In another embodiment, only one transducer element serves for oscillation detection.

In an additional embodiment, in each case, two transducer elements serve for producing oscillations and the remaining element serves for detection. In such case, for example, the task of producing, or detection, is fulfilled by, in each case, another transducer element. This permutation of the tasks occurs in such case in normal measurement operation (i.e. measuring mode and test mode run simultaneously) or during special test phases with the test mode.

In an additional variant of the invention, it is provided, that the tasks of the transducer elements rotate.

Figure 2:
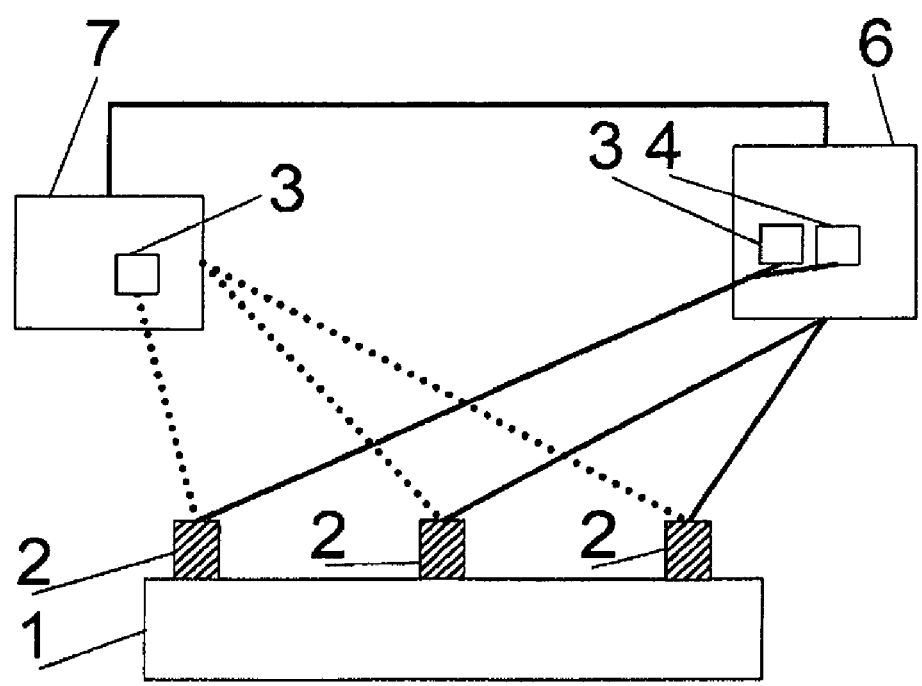
FIG. 2 is a schematic drawing of a second embodiment of a measuring device of the invention.

FIG. 2 shows, schematically presented, a second variant of the embodiment of the measuring device.

Each of the three transducer elements 2 is, on the one hand, connected with the test control unit 6 and, on the other hand, with the measurement control unit 7. Thus, it is possible, that one electronics 7 controls only the measuring and another electronics 6 only the test. At the same time, there is a connection between the test control unit 6 and the measurement control unit 7, so that alignment between these two units is possible, i.e. it is, for example, coordinated, that the two modes take place correspondingly at the same time or offset in time or that a corresponding mutual influencing of the measured values is taken into consideration.

Considered here is the inflow side, transducer element 2, which is located here to the left in the figure. This transducer element 2 is connected with an oscillation driving electronics 3 in the measurement control unit 7. I.e., in the measurement control unit 7 are located the electronic units, which operate the individual transducer elements 2, thus either with supply of an exciter signal or receipt of an electrical, received signal, in each case provided with a fixed task.

The transducer element 2 is, on the other hand, connected in the test control unit 6 both with oscillation driving electronics 3, as well as also with oscillation receiving electronics 4. Provided in the test control unit 6 for this is, for example, a corresponding switch unit, which establishes, in each case, the connection of the transducer element 2 to one of the two operating electronics 3, 4.

The same is true, as regards the connections with the electronic units for operating the transducer elements, also for the other participating transducer elements. I.e., in the measurement control unit 7 there is in each case a fixed connection between operating electronics: Either oscillation driving electronics 3, or oscillation receiving electronics 4, and transducer element 2. In the test control unit 6, in contrast, there are also different combinations, i.e. the transducer elements are connected in an embodiment in the test control unit 6 variably with different electronics.

The connection in the test control unit 6 both with oscillation driving electronics 3, as well as also with oscillation receiving electronics 4, permits, thus, for example, the individual transducer elements 2, in each case, to cover different tasks: Either oscillation excitement or oscillation detection.

Thus, the transducer elements 2 fulfill, through their connection with the respective electronics in the measurement control unit 7, in the measuring mode, in each case, a fixedly assigned task (production or detection of oscillations). And, by the different connections in the test control unit 6, the transducer elements can in the test mode execute in each case a different task. In the test mode, by this embodiment, then also asymmetries or special phases of the mechanics of the measuring apparatus can be measured.

Figure 3:
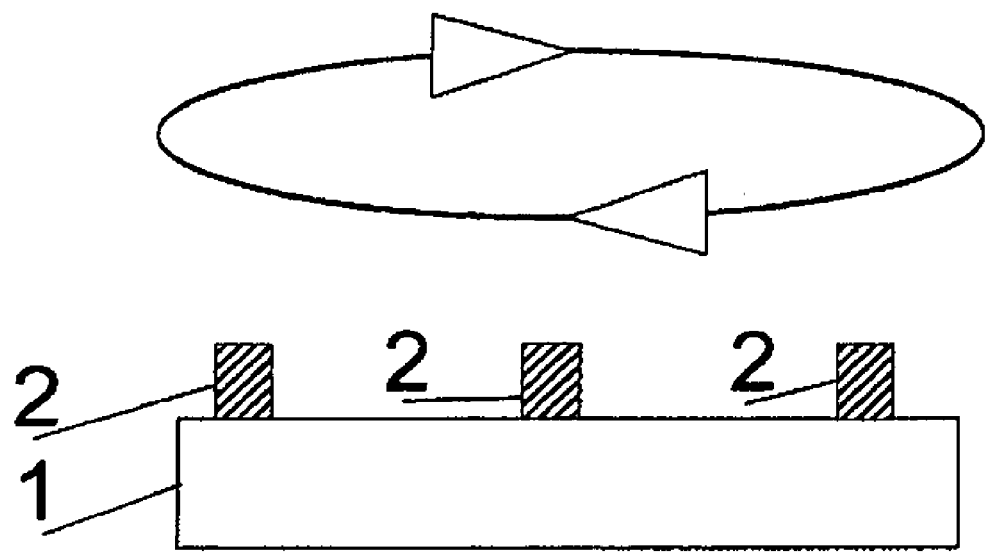
FIG. 3 is a schematic drawing of the permutation of the tasks of the transducer elements.

FIG. 3 shows, schematically, how, for example, the task of oscillation excitation is rotated through the three transducer elements 2 of this embodiment. In an embodiment, in each case, one transducer element 2 is responsible for the oscillation excitation, wherein this task is alternately performed, in each case, by another transducer element 2. In a second embodiment, in each case, two transducer elements 2 are enlisted for oscillation production, wherein the combining to these pairs is likewise permutated through the three available elements 2. The task of oscillation receipt is assigned to the transducer elements 2 complementarily thereto.

The tasks, or functions, of the transducer elements rotate— here as symbolized by the arrow—, thus, e.g. in the test phase, over the individual transducer elements, wherein the functions are, in each case, performed individually or in groups.

The invention claimed is:

1. A method for measuring and/or monitoring at least one flow parameter of a medium, which medium flows through a measuring tube, wherein at least two transducer elements contact the measuring tube, comprising the steps of:
   the measuring tube is excitable to execute mechanical oscillations and by means of which mechanical oscillations tube are receivable, and
   each of the at least two transducer elements is applied, offset in time, alternately, for exciting the measuring tube to execute mechanical oscillations and for receiving the mechanical oscillations of the measuring tube.

2. The method as claimed in claim 1, wherein:
   the transducer element is operated, offset in time, or simultaneously, in a test mode and in a measuring mode.

3. The method as claimed in claim 1, further comprising the step of:
   the transducer element is supplied in the test mode with a test exciter signal and in the measuring mode with a measuring exciter signal.

4. The method as claimed in claim 3, wherein:
   said test exciter signal and said measuring exciter signal differ from one another, at least as regards frequency.

5. The method as claimed in claim 1, wherein:
   the measuring tube is excited, through the transducer element in combination with an oscillation driving electronics, to execute mechanical oscillations, and through the transducer element, in combination with oscillation receiving electronics different from the oscillation driving electronics, mechanical oscillations of the measuring tube are received.

6. The method as claimed in claim 1, wherein:
   the measuring tube is excited, through at least two transducer elements, alternately, to execute mechanical oscillations and mechanical oscillations are received from the measuring tube;
   in each case, one transducer element excites the measuring tube to execute mechanical oscillations and the other transducer element receives mechanical oscillations of the measuring tube.

7. The method as claimed in claim 1, wherein:
   the measuring tube is excited, through at least three transducer elements, individually or, especially, grouped pairwise, alternately, to execute mechanical oscillations and mechanical oscillations are received from the measuring tube; and
   in each case, at least one transducer element excites the measuring tube to execute mechanical oscillations and at least one transducer element receives mechanical oscillations of the measuring tube.

8. The method as claimed in claim 7, wherein:
   the measuring tube is excited, in each case, alternately, through one of the three transducer elements, to execute mechanical oscillations, and the mechanical oscillations of the measuring tube are received by two transducer elements.

9. The method as claimed in claim 7, wherein:
   the measuring tube is excited, in each case, alternately, through, two of the three transducer elements, to execute mechanical oscillations, and the mechanical oscillations of the measuring tube are received by one transducer element.

10. An apparatus for measuring and/or monitoring at least one flow parameter of a medium, which medium flows through a measuring tube, which apparatus comprises:
    at least one transducer element, via which the measuring tube is both excitable to execute mechanical oscillations, as well as mechanical oscillations of the measuring tube are receivable;
    at least one oscillation driving electronics connected to said at least one transducer element; and
    one oscillation receiving electronics, wherein:
    said oscillation driving electronics and said oscillation receiving electronics are different from one another;
    said oscillation driving electronics effects, that said at least one transducer element excites the measuring tube to execute mechanical oscillations; and
    said oscillation receiving electronics effects, that said at least one transducer element receives mechanical oscillations from the measuring tube.

11. The apparatus as claimed in claim 10, further comprising:
    at least one test control unit, which operates at least said at least one transducer element in a test mode; and
    at least one measurement control unit which operates said at least one transducer element in a measuring mode.

12. The apparatus as claimed in claim 10, wherein:
    at least two transducer elements are provided, via which transducer elements both the measuring tube is excitable to execute mechanical oscillations, as well as mechanical oscillations of the measuring tube are receivable.

13. The apparatus as claimed in claim 10, wherein:
    at least three transducer elements are provided, via which transducer elements both the measuring tube is excitable to execute mechanical oscillations, as well as mechanical oscillations of the measuring tube are receivable.

14. The apparatus as claimed in claim 10, wherein:
    at least two transducer elements are, in each case, connected with said at least one oscillation driving electronics and said oscillation receiving electronics; and
    said at least one oscillation driving electronics and said oscillation receiving electronics are, in each case, different from one another.

15. The apparatus as claimed in claim 13, wherein:
two transducer elements are placed symmetrically to the third transducer element on the measuring tube.

16. The apparatus as claimed in claim 10, further comprising:
at least one control unit, which control unit, via said at least one oscillation driving electronics and the therewith connected transducer element, excites the measuring tube to execute mechanical oscillations and which control unit, via said at least one oscillation receiving electronics and the therewith connected transducer element, receives the mechanical oscillations of the measuring tube.

* * * * *